US009790129B2

(12) United States Patent
    Carden

(10) Patent No.: US 9,790,129 B2
(45) Date of Patent: Oct. 17, 2017

(54) METHOD OF FABRICATING HIGH LIGHT TRANSMISSION ZIRCONIA BLANKS FOR MILLING INTO NATURAL APPEARANCE DENTAL APPLIANCES

(71) Applicant: James R. Glidewell Dental Ceramics, Inc., Newport Beach, CA (US)

(72) Inventor: Robin A. Carden, San Juan Capistrano, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 15/220,849

(22) Filed: Jul. 27, 2016

(65) Prior Publication Data

US 2016/0332918 A1    Nov. 17, 2016

Related U.S. Application Data

(63) Continuation of application No. 13/481,810, filed on May 26, 2012, now Pat. No. 9,434,651.

(51) Int. Cl.
    *C04B 35/26* (2006.01)
    *A61C 13/083* (2006.01)
    (Continued)

(52) U.S. Cl.
    CPC .......... *C04B 35/62625* (2013.01); *A61C 5/77* (2017.02); *A61C 13/0004* (2013.01);
    (Continued)

(58) Field of Classification Search
    CPC ....................... C04B 35/486; C04B 35/62635
    (Continued)

(56) References Cited

U.S. PATENT DOCUMENTS 3,111,396 A * 11/1963 Ball ................ B01D 39/20
                                              264/628
3,523,916 A *  8/1970 Hill ................... C08J 3/203
                                              220/62.11
(Continued)

FOREIGN PATENT DOCUMENTS

CN    1215711 A    5/1999
CN    1236761 A   12/1999
(Continued)

OTHER PUBLICATIONS

International Search Report issued in application PCT/US2008/12489 dated Dec. 31, 2008.
(Continued)

*Primary Examiner* — Nahida Sultana
(74) *Attorney, Agent, or Firm* — Dianne Burkhard

(57) ABSTRACT

A process for fabricating pre-sintered zirconia blanks that are then computer machined and sintered to form dental appliances having highly advantageous features. The principal steps of a preferred embodiment of that process comprise; a) preparing a ceramic slurry of zirconia powder; b) subjecting the slurry to attrition milling down to about a 5-29 nm crystallite size; c) preparing a vacuum assisted and pressure assisted slip casting mold and pouring the milled slurry into the slip-casting mold; d) after casting, excess slurry is poured from the mold and a consolidated zirconia blank is removed; e) drying the blank and pre-sintering it to form solid blanks ready for CAD/CAM machining and sintering to net shape. The attrition is run with ball bearings that are of the sample material to prevent contamination. It also is run, up to 24 hours, to break down the crystallites to overcome the high density of zirconia.

19 Claims, 6 Drawing Sheets

(51) Int. Cl.
*C04B 35/486* (2006.01)
*C04B 35/626* (2006.01)
*A61C 13/00* (2006.01)
*A61C 13/08* (2006.01)
*A61C 5/77* (2017.01)

(52) U.S. Cl.
CPC ...... *A61C 13/0006* (2013.01); *A61C 13/0022* (2013.01); *A61C 13/082* (2013.01); *A61C 13/083* (2013.01); *C04B 35/486* (2013.01); *C04B 35/62635* (2013.01); *C04B 2235/549* (2013.01); *C04B 2235/5454* (2013.01); *C04B 2235/6026* (2013.01); *C04B 2235/6027* (2013.01); *C04B 2235/612* (2013.01)

(58) Field of Classification Search
USPC ..... 264/17, 667, 654, 16, 299, 637, 651, 86, 264/636; 419/45
See application file for complete search history.

(56) References Cited

U.S. PATENT DOCUMENTS

| | | | |
|---|---|---|---|
| 3,837,825 A * | 9/1974 | Loxley | C03B 19/06 264/662 |
| 4,431,420 A | 2/1984 | Adair | |
| 4,556,530 A * | 12/1985 | van der Scheer | B01D 69/122 210/500.27 |
| 4,769,349 A | 9/1988 | Hillig et al. | |
| 4,772,436 A | 9/1988 | Tyszblat | |
| 4,828,495 A | 5/1989 | Bell et al. | |
| 4,906,424 A * | 3/1990 | Hughes | B22F 1/0059 264/328.18 |
| 4,983,182 A | 1/1991 | Kijima et al. | |
| 5,185,177 A | 2/1993 | Kijima et al. | |
| 5,192,325 A | 3/1993 | Kijima et al. | |
| 5,203,936 A | 4/1993 | Dolhert | |
| 5,256,609 A | 10/1993 | Dolhert | |
| 5,296,175 A | 3/1994 | Iwasaki et al. | |
| 5,342,564 A | 8/1994 | Wei | |
| 5,372,178 A | 12/1994 | Claar | |
| 5,395,437 A | 3/1995 | Chiou | |
| 5,441,408 A | 8/1995 | Moschik | |
| 5,443,770 A | 8/1995 | Kristic et al. | |
| 5,672,055 A | 9/1997 | Koutavas | |
| 5,776,382 A | 7/1998 | Kim et al. | |
| 5,785,911 A | 7/1998 | Willkens et al. | |
| 5,788,891 A * | 8/1998 | Gauckler | C04B 35/111 264/299 |
| 5,843,348 A | 12/1998 | Giordano | |
| 5,849,068 A | 12/1998 | Hoffmann et al. | |
| 5,975,905 A | 11/1999 | Kim et al. | |
| 6,007,926 A | 12/1999 | Provenzano et al. | |
| 6,180,034 B1 | 1/2001 | Buck et al. | |
| 6,200,526 B1 * | 3/2001 | Fox | C04B 41/5155 264/650 |
| 6,291,378 B1 | 9/2001 | Evans | |
| 6,431,800 B1 | 8/2002 | Suzuki | |
| 6,814,917 B1 | 11/2004 | Watanabe et al. | |
| 6,878,456 B2 | 4/2005 | Castro | |
| 6,896,846 B1 | 5/2005 | Varma | |
| 6,946,013 B2 | 9/2005 | Alward et al. | |
| 8,178,012 B1 | 5/2012 | Khan | |
| 8,196,755 B2 * | 6/2012 | Diefenbacher | B01D 53/228 210/490 |
| 8,268,230 B2 | 9/2012 | Cherepy | |
| 8,572,484 B2 * | 10/2013 | Maruyama | H04N 1/00456 358/1.16 |
| 8,785,518 B2 * | 7/2014 | Suh | C08F 2/48 433/228.1 |
| 8,813,364 B2 * | 8/2014 | Schechner | A61C 13/0004 264/16 |
| 9,039,947 B2 | 5/2015 | Jahns | |
| 9,193,630 B2 * | 11/2015 | Bocciarelli | C04B 35/4885 |
| 9,309,155 B2 * | 4/2016 | Nahas | C04B 35/591 |
| 9,434,651 B2 | 9/2016 | Carden | |
| 2001/0048969 A1 | 12/2001 | Constantino et al. | |
| 2002/0037800 A1 | 3/2002 | Yang | |
| 2002/0155412 A1 | 10/2002 | Panzera et al. | |
| 2003/0096214 A1 | 5/2003 | Luthardt et al. | |
| 2004/0119180 A1 | 6/2004 | Frank et al. | |
| 2005/0023710 A1 | 2/2005 | Brodkin | |
| 2005/0203231 A1 | 9/2005 | Halpert et al. | |
| 2006/0014390 A1 | 1/2006 | Lee et al. | |
| 2007/0056467 A1 | 3/2007 | Panzera | |
| 2007/0134496 A1 | 6/2007 | Katagiri et al. | |
| 2008/0085828 A1 | 4/2008 | Khan et al. | |
| 2008/0164402 A1 | 7/2008 | Menke | |
| 2008/0258358 A1 | 10/2008 | Oswald et al. | |
| 2009/0098365 A1 | 4/2009 | Moeltgen | |
| 2009/0115084 A1 | 5/2009 | Moon | |
| 2009/0220787 A1 | 9/2009 | Bernard-Granger et al. | |
| 2009/0291011 A1 | 11/2009 | Zhang et al. | |
| 2009/0321971 A1 | 12/2009 | Brodkin et al. | |
| 2010/0003157 A1 | 1/2010 | Scholl et al. | |
| 2010/0249305 A1 * | 9/2010 | Laubersheimer | B28B 1/00 524/403 |
| 2011/0236860 A1 | 9/2011 | Jahns | |
| 2011/0260349 A1 | 10/2011 | Rolf et al. | |
| 2012/0193823 A1 | 8/2012 | Goetzinger | |
| 2013/0224454 A1 | 8/2013 | Jung | |
| 2013/0224688 A1 | 8/2013 | Mayr | |
| 2013/0341812 A1 | 12/2013 | Schechner | |
| 2014/0008826 A1 * | 1/2014 | Dierkes | A61C 13/0004 264/16 |

FOREIGN PATENT DOCUMENTS

| | | |
|---|---|---|
| DE | 1471423 B | 12/1969 |
| EP | 0329284 | 9/1992 |
| JP | 411019910 A | 1/1999 |
| WO | WO2006024098 A1 | 3/2006 |
| WO | WO2007000310 A1 | 4/2007 |

OTHER PUBLICATIONS

U.S.P.T.O Non-Final Office Action issued in U.S. Appl. No. 12/290,089 dated Jun. 2, 2009.
U.S.P.T.O Non-Final Office Action issued in the U.S. Appl. No. 12/290,089 dated Dec. 1, 2009.
International Search Report in International Application No. PCT/US2013/041941 dated Oct. 24, 2013.
Non-Final Office Action issued in U.S. Appl. No. 13/481,810 dated Jan. 15, 2016.
Final Office Action issued in U.S. Appl. No. 13/481,810 dated Sep. 22, 2015.
Non-Final Office Action issued in U.S. Appl. No. 13/481,810 dated Mar. 12, 2015.
Non-Final Office Action issued in U.S. Appl. No. 13/481,810 dated Aug. 22, 2014.

* cited by examiner

METHOD OF FABRICATING HIGH LIGHT TRANSMISSION ZIRCONIA BLANKS FOR MILLING INTO NATURAL APPEARANCE DENTAL APPLIANCES

CROSS-REFERENCE TO RELATED APPLICATIONS

This application is a continuation of, and claims priority to, U.S. patent application Ser. No. 13/481,810, filed May 26, 2012, which is hereby incorporated by reference in its entirety.

BACKGROUND OF THE INVENTION

1. Field of the Invention

The present invention relates generally to the manufacture of ceramic dental appliances such as crowns and bridges. The invention herein is related more particularly to the milling of zirconia blanks into such appliances where the blanks are fabricated by a vacuum and pressure assisted slip-casting method to achieve superior physical properties.

2. Background Art

Dental prosthetic devices or appliances must satisfy a number of different criteria. They need to have excellent physical properties (Flexural Strength to 1600 MPa) to resist wear and mechanical deformation for very long periods of time. They should also provide good aesthetic characteristics which mean that they have a natural appearance in color, texture and shape so that they are not readily distinguishable from the original natural teeth. They should also be readily fabricated at reasonable cost which means that the cost of materials used and the time required in their manufacture, should be within reasonable limits.

Dental appliances made of zirconia can meet these criteria. It is a ceramic material which can be made to be extremely hard and fracture resistant. Applicant has discovered that if provided in pre-fabricated pre-sintered blanks, they can be readily machined in CAD/CAM systems and then sintered with highly predictable shrinkage to conform to virtually any desired dental appliance shape with high yield and minimal manual intervention. A key aspect of the aesthetic appearance of zirconia dental appliances would be achieved if it were possible to provide such prosthetic devices with a substantial degree of light transmissivity. Translucent appliances would exhibit the color of the underlying natural dental material and thus go a long way toward achieving a highly desirable appearance, i.e., that is matched to the color of adjacent natural teeth. Thus, if it were possible to provide pre-fabricated, pre-sintered zirconia blanks and yet still retain the advantageous mechanical and easy fabrication properties of the ceramic, that would be a significant accomplishment in the art of dental appliances. Even though Applicant is not the first to consider slip-casting zirconia for the dental appliance art (see U.S. Pat. No. 4,772,436 to Tyszblat or U.S. Pat. No. 5,975,905 to Kim et al), there is no known relevant prior art which discloses all of the process steps of the present invention for fabricating a pre-sintered zirconia blank for the dental appliance arts. Moreover, Tyszblat teaches the interlacing of fitted metal oxide particles in tine solid phase and glass. Kim et al discloses the creation of a ceramic sheet of thickness 0.1 mm to 1.0 mm and then coating the sheet onto a gypsum mold under heat and pressure and then, after sintering, coating the resultant body with glass powder. No other known partially stabilized zirconia material can be made to reach a stiffness of 1600 MPa mark when slip cast. No other known partially stabilized zirconia material reaches the high degree of light transmission in the 500-800 nm wavelength, which is needed to transmit the warm colors of the mouth. The partially stabilized zirconia is normally very hard to slip cast with a high density of 6.03 g/cc. Aluminum oxide for example is readily slip cast because of its lower density 3.98 g/cc. Any ceramic with density between 2.0 and 4.0 g/cc is more readily made by a slip cast process. This is because the lower density allows the particulate to stay dispersed longer which results in better green density and strength after final sintering. When densities rise above 4 g/cc, high strength is never reached in colloidal processing. Very high density materials normally cannot be cast at all, such as tungsten carbide at 14.6 g/cc.

SUMMARY OF THE INVENTION

The present invention comprises a process for fabricating pre-sintered zirconia blanks that are then computer machined and sintered to form translucent dental appliances having highly advantageous features. The principal steps of a preferred embodiment of that process comprise a) preparing a ceramic slurry of binderless zirconia powder; b) subjecting the slurry to attrition milling for an extended time of up to 24 hours to achieve a crystallite size in the range of about 5 nm to about 29 nm; c) preparing a vacuum assisted and optional pressure assisted slip casting mold and pouring the milled slurry into the slip-casting mold; d) after casting, excess slurry is poured from the mold and a consolidated zirconia blank is removed; e) drying the blank and pre-sintering it to form solid blanks ready for CAD/CAM machining and sintering to net shape. In the preferred embodiment of the process herein, the zirconia powder is dispersed in deionized water using a dispersant chemical solution such as tetramethyl ammonium hydroxide to adjust the pH of the slurry and thus homogeneously disperse the zirconia powder. Other dispersants such as polyisobutylene, various acid salts, bases and certain oils, may also serve as dispersant chemicals. The present invention achieves extremely high flexural strength and unusually high translucency by employing zirconia fabricated by a slip cast method in which the crystallite size is in the range of about 5 nm to about 29 nm to overcome the inherent high density of zirconia. The uniquely achieved flexural strength and translucency are particularly important in the field of dental restorations such as crowns and bridges where resistances to bite pressure and material appearance are critical.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF A PREFERRED EMBODIMENT

Figure 1:
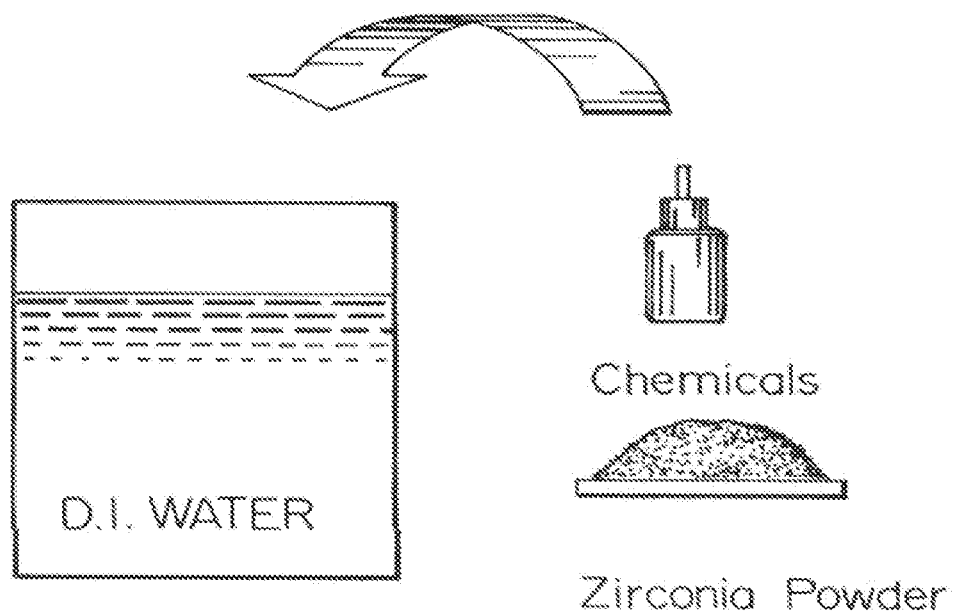
FIG. 1 shows the slurry preparation process by mixing zirconia powder and chemicals (either a dispersant or a chemical that controls PH) into deionized water.
Figure 2:
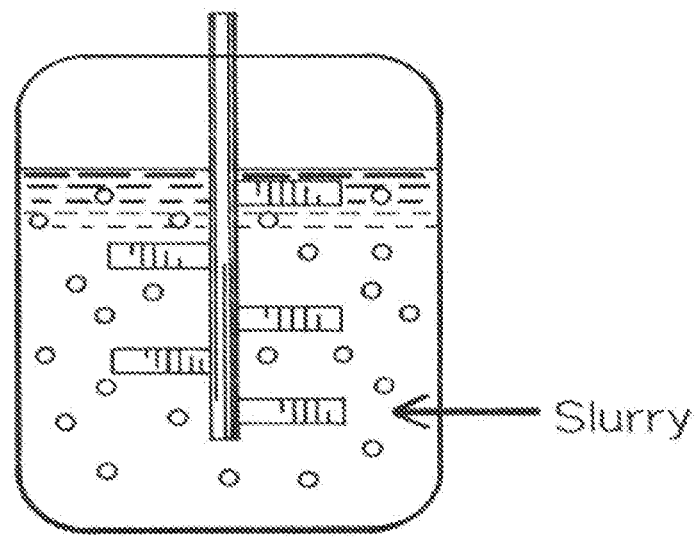
FIG. 2 represents the attrition milling step.
Figure 3:
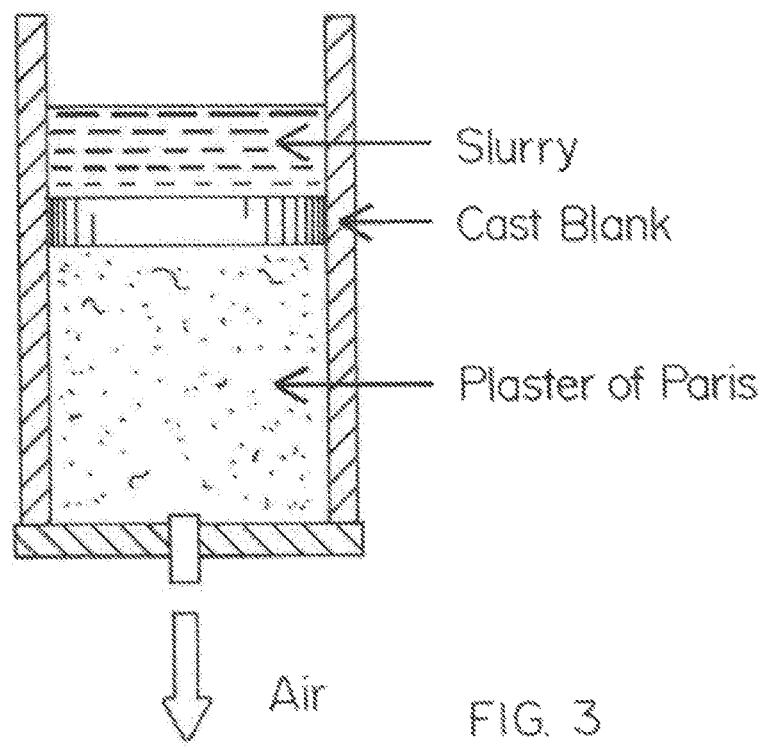
FIG. 3 represents the vacuum slip casting step of the invention.
Figure 4:
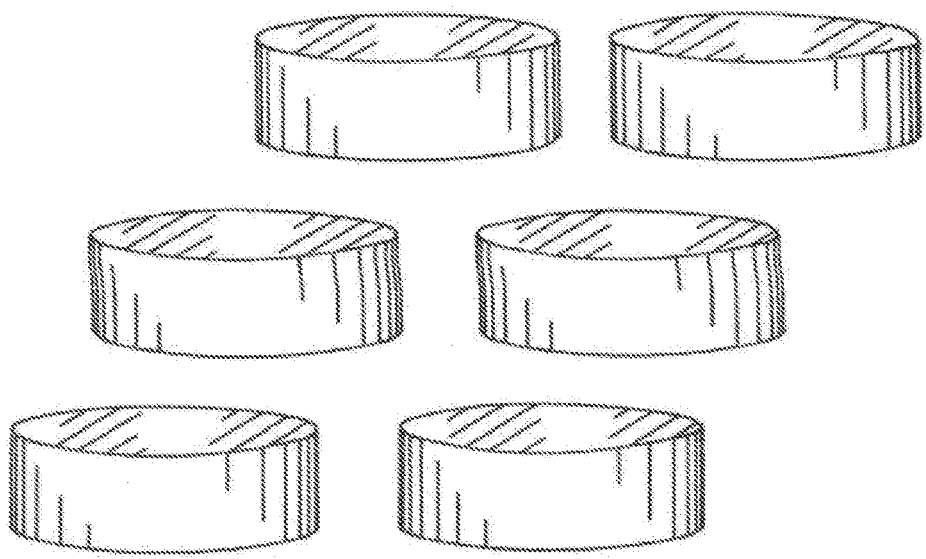
FIG. 4 shows the drying step of the invention.
Figure 5:
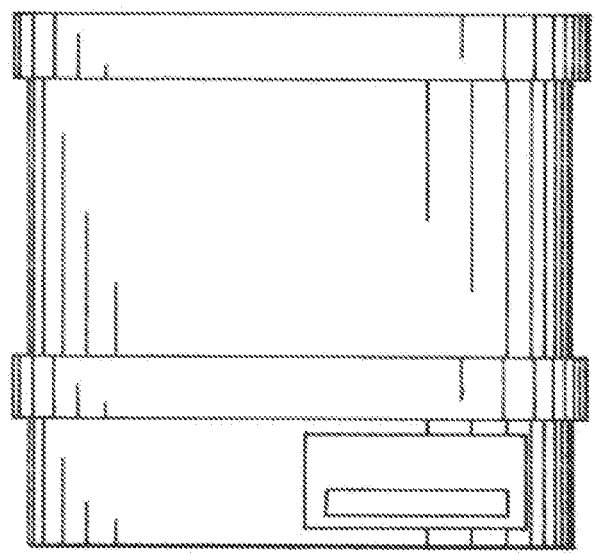
FIG. 5 shows the pre-sintering step of the inventive process hereof.
Figure 6:
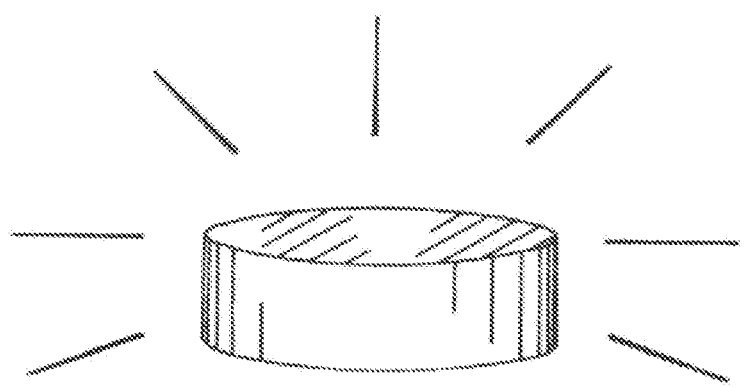
FIG. 6 represents the completed pre-sintered zirconia blank ready to be machined in a CAD/CAM system.
Figure 7:
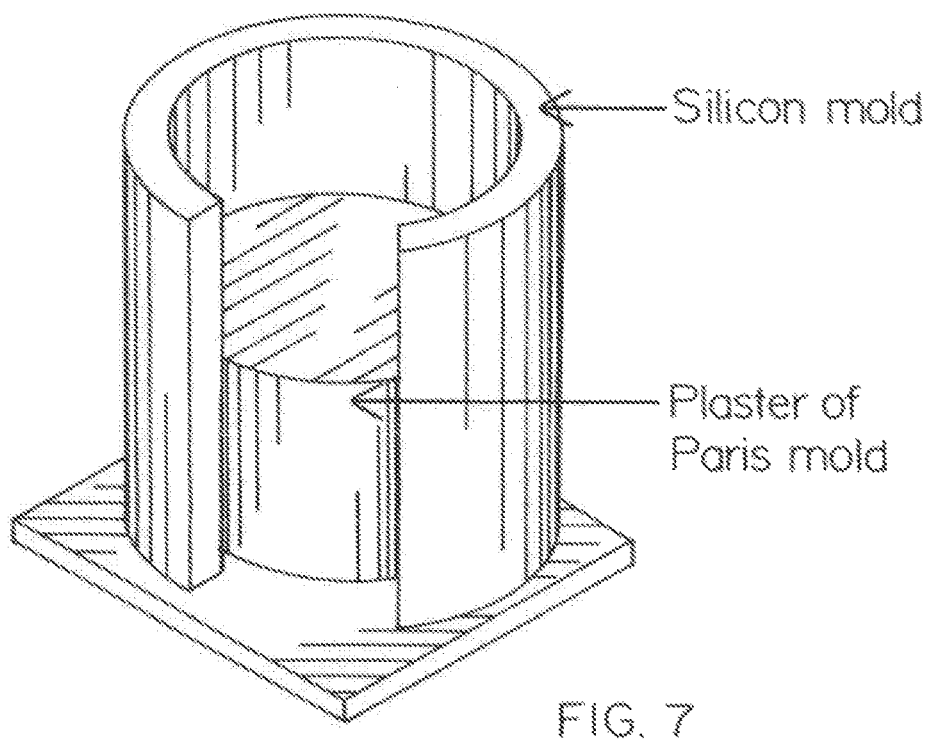
FIGS. 7 to 8 illustrate in some added detail, the slip-casting step of FIG. 3.
Figure 8:
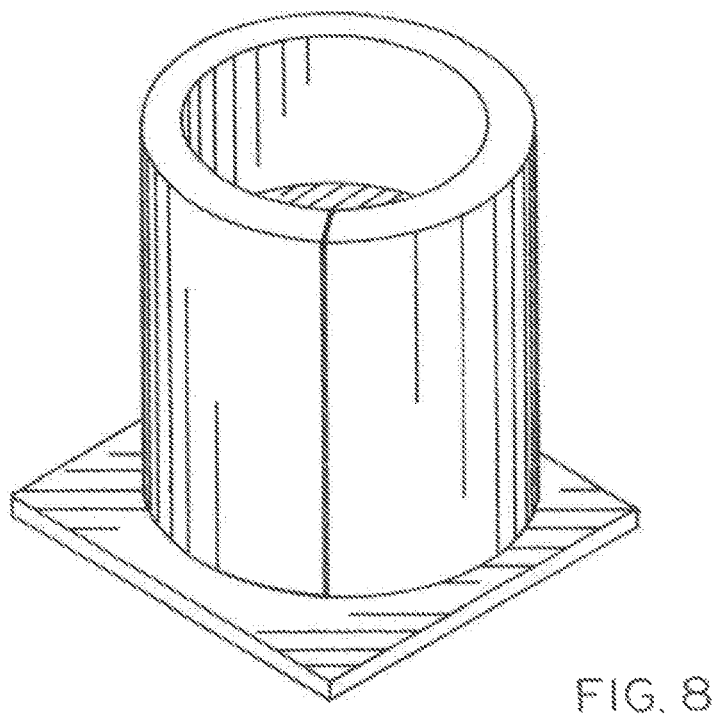

Referring to the accompanying drawings and initially to FIGS. 1 to 6, it will be seen that the present invention is a process comprising the following steps:

a) The zirconia powder is dispersed into de-ionized water using either polymer dispersants or by controlling pH with base/acid. The slurry is preferably ultra-sonicated to remove soft agglomerates and for better mixing (see FIG. 1).

b) Attrition milling the prepared slurry, preferably in a zirconia bowl (see FIG. 2) until the crystallite size is in the range of about 5 nm to about 29 nm.

c) Slip-casting the milled slurry by preparing a porous plaster of paris mold. An organic polymer mold may be substituted for the plaster of paris mold. Placing the plaster of paris mold within a surrounding silicone mold enclosure (or enclosure of a rubber or other elastic polymer material, see FIGS. 11A and 11B) and softly tightening the enclosure around the plaster of paris to form a leak-proof system (see FIGS. 7 and 8). In the preferred embodiment, the enclosure is secured by rubber bands or pipe ties (see FIG. 9). Attaching to a bottom surface aperture of the enclosure, a vacuum line to suck out excess liquid (i.e., water) (see FIG. 10). A vacuum pressure of −5 to −40 psi is preferred. Pouring the slurry into the enclosure above the plaster of paris mold. Eventually a slip-cast zirconia blank will form above the plaster of paris mold. This blank is removed by pouring out the excess slurry and opening the silicone mold to permit removal of the plaster of paris mold and zirconia blank. An optional positive pressure may be applied above the enclosure to further promote the process. A positive pressure of 1 to 30 psi is preferred.

d) Each removed zirconia blank is allowed to dry at room temperature preferably using gently circulating air at low humidity (see FIG. 4). The zirconia blocks are then pre-sintered at 850° C. to 1200° C. for about two hours (see FIG. 5). The fully dried zirconia blanks are ready for computer-controlled milling and sintering to net shape (see FIG. 6).

Figure 9A:
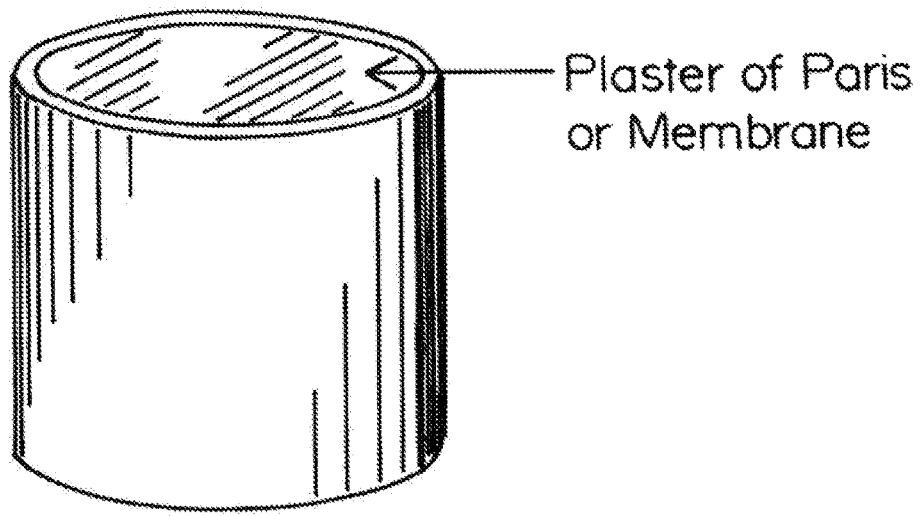
FIGS. 9A and 9B show an optional added slip casting step using a polymer sleeve enclosed plaster of paris mold to protect the delicate plaster of paris material during handling.
Figure 9B:
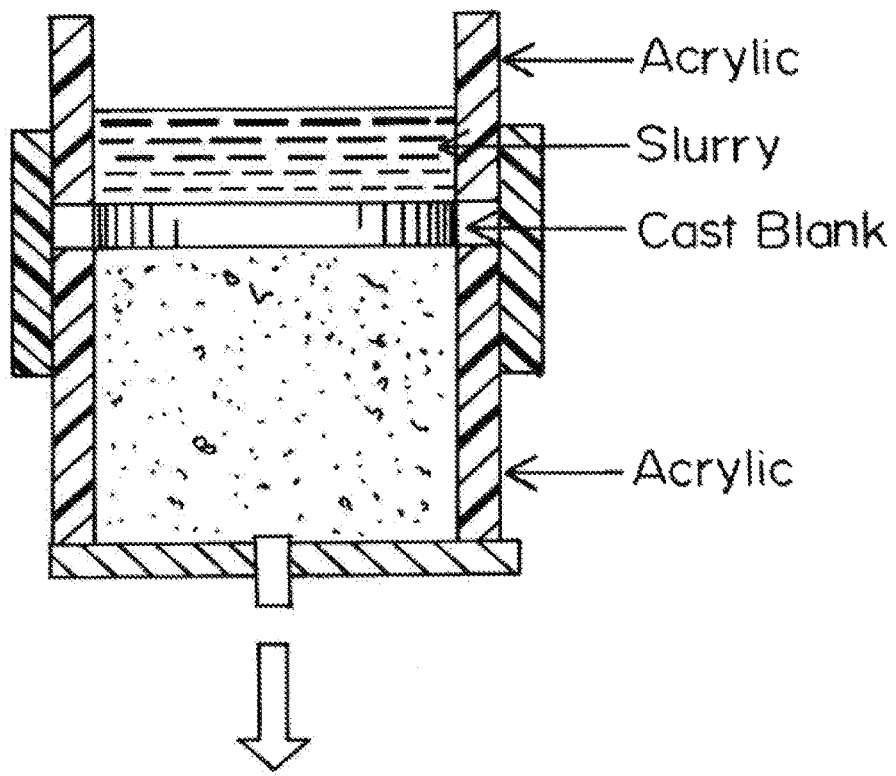

As shown in FIGS. 9A and 9B, the plaster of paris mold may be protected from handling damage by enclosing its radial surface in a plastic or polymer sleeve.

Figure 10:
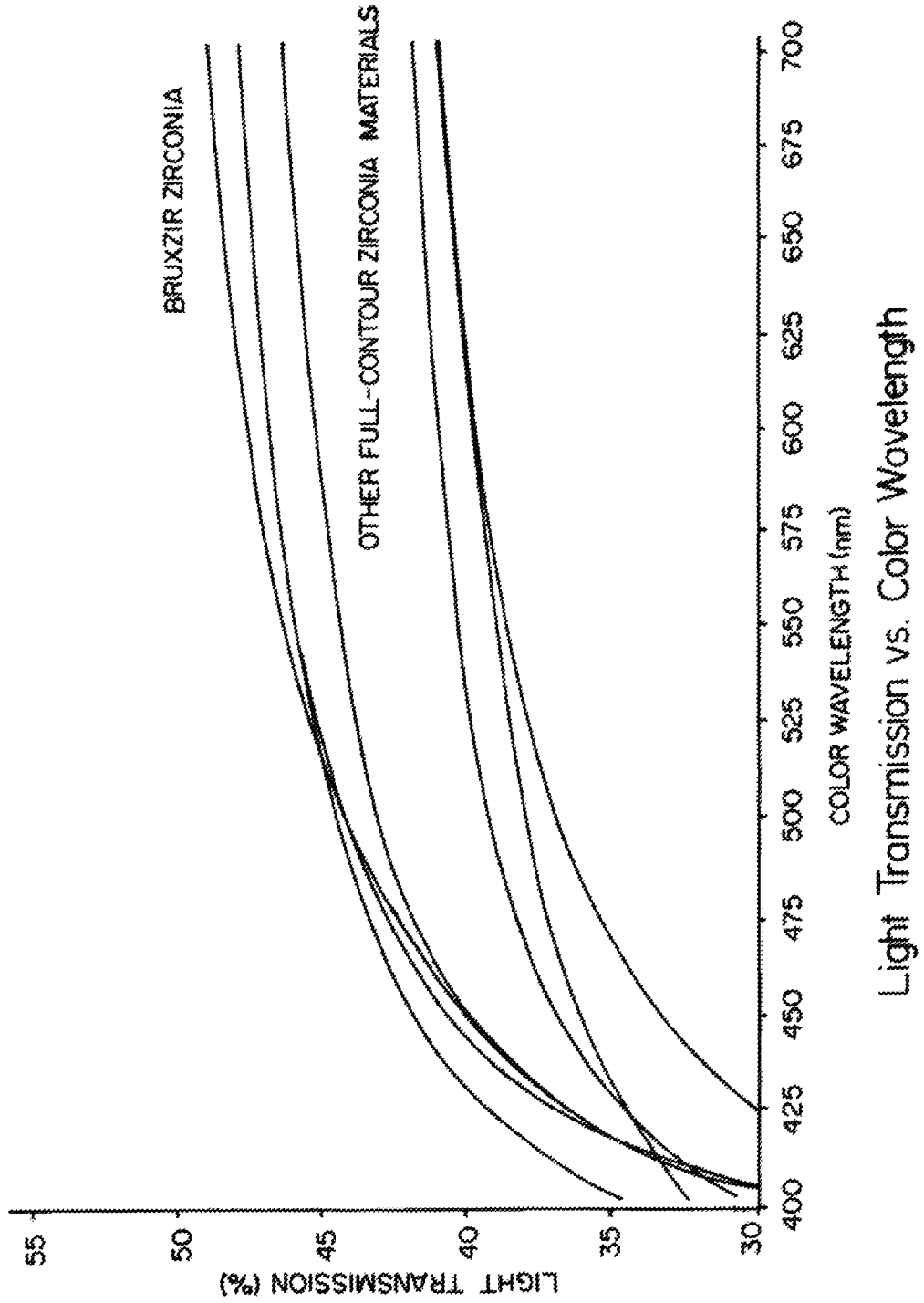
FIG. 10 is a graphical illustration of light transmission versus color wavelength for zirconia that is fabricating using the method of the invention and for zirconia made by more conventional methods.

FIG. 10 shows graphically the favorable light transmission characteristics of zirconia restorations made according to the preferred embodiment hereof and compares such characteristics to more conventionally fabricated zirconia restorations as a function of wavelength.

It will now be understood that the present invention comprises a process for preparing zirconia blanks for milling into dental appliance shapes using CAD/CAM control and then sintering the shaped zirconia appliances to net shape.

Although a preferred embodiment has been disclosed herein, it will now be apparent that various modifications may be made to the various steps hereof without deviating from the principal inventive features hereof. Accordingly, the scope of the invention is to be limited only by the appended claims and to their equivalents.

I claim:

1. A method of fabricating a pre-sintered, ceramic zirconia blank for use in fabricating a dental appliance, comprising:
   obtaining a zirconia ceramic slurry having a ceramic crystallite size in the range of about 5 nm to about 29 nm comprising zirconia powder, water and a dispersant to disperse the ceramic zirconia powder in water;
   pouring the zirconia ceramic slurry into a vacuum-assisted slip-casting assembly comprising a mold; and
   consolidating the zirconia ceramic slurry to form a pre-sintered zirconia blank that is shapeable into a dental appliance shape by a consolidation process consisting essentially of the steps of
     removing water from the zirconia ceramic slurry, by applying to one end of the vacuum-assisted slip-casting assembly an evacuating pressure in the range of −5 to −40 psi and optionally, applying a positive pressure in the range of 1 to 30 psi to another end of the vacuum-assisted slip-casting assembly, to form a consolidated ceramic zirconia blank,
     drying the zirconia blank, and
     pre-sintering the zirconia blank to form a shapeable, pre-sintered zirconia blank.

2. A method of fabricating a binderless, ceramic zirconia blank for use in fabricating a dental appliance, comprising:
   obtaining a binderless, zirconia ceramic slurry having a crystallite size in the range of about 5 nm to about 29 nm comprising binderless, zirconia powder, water and a dispersant to disperse the binderless, zirconia powder in water;
   pouring the zirconia ceramic slurry into a vacuum-assisted slip-casting assembly comprising a mold; and
   consolidating the zirconia ceramic slurry to form a ceramic zirconia blank that is shapeable into a dental appliance shape, by a consolidation process consisting essentially of the steps of removing water from the binderless, zirconia ceramic slurry by applying to one end of the vacuum-assisted slip-casting assembly an evacuating pressure in the range of −5 to −40 psi and optionally, applying a positive pressure in the range of 1 to 30 psi to another end of the vacuum-assisted slip-casting assembly, to form a consolidated binderless, ceramic zirconia blank in the mold.

3. The method of claim 2, further comprising the step of pre-sintering the binderless ceramic zirconia blank to form a shapeable, pre-sintered binderless zirconia blank.

4. The method of claim 1, wherein the zirconia ceramic slurry that is poured into the mold comprises particulate, and the particulate consists essentially of metal oxides.

5. The method of claim 2, wherein the vacuum-assisted slip-casting assembly comprises a porous plaster of paris mold.

6. The method of claim 5, wherein a polymer sleeve is in radial surrounding engagement with a plaster of paris mold.

7. The method of claim 2, wherein the vacuum-assisted slip-casting assembly comprises an organic polymer mold or membrane.

8. The method of claim 2, wherein the zirconia powder is dispersed by controlling the pH with a base.

9. The method of claim 2, wherein the zirconia powder is dispersed by controlling the pH with a base having a pH in the range of 9.5 to 12.

10. The method of claim 2, wherein the zirconia is dispersed by controlling the pH with an acid.

11. The method of claim 2, wherein the zirconia is dispersed by controlling the pH with an acid having a pH in the range of 1 to 3.9.

12. The method of claim 2, wherein the dispersant is tetramethyl ammonium hydroxide.

13. The method of claim 2, wherein the dispersant is a polymer dispersant.

14. The method of claim 2, wherein the dispersant is polyisobutylene.

15. The method of claim 2 further comprising the step of pre-sintering the ceramic zirconia blank, and shaping the pre-sintered ceramic zirconia blank into a dental appliance form after the step of pre-sintering.

16. A method of fabricating a binderless, ceramic zirconia blank for use in fabricating a dental appliance, comprising:
    attrition milling a ceramic slurry comprising a binderless, zirconia powder dispersed in water with a dispersant to form a dispersed zirconia ceramic slurry having a crystallite size in the range of about 5 nm to about 29 nm;
    pouring the milled ceramic slurry into a vacuum-assisted slip-casting assembly comprising a mold, wherein the zirconia ceramic slurry that is poured into the mold comprises a particulate, and the particulate consisting essentially of metal oxide; and
    removing water from the milled ceramic slurry and consolidating the zirconia ceramic in the mold by applying to one end of the vacuum-assisted slip-casting assembly an evacuating pressure in the range of −5 to −40 psi, to form a consolidated binderless, ceramic zirconia blank in the mold.

17. The method of claim 1, wherein the zirconia ceramic slurry that is poured into the mold comprises particulate, and the particulate consists essentially of zirconia ceramic material.

18. The method of claim 16, wherein the step of attrition milling comprises using a zirconia bowl.

19. The method of claim 16, further comprising the step of ultra-sonicating the zirconia ceramic slurry to remove agglomerates.

* * * * *